(12) United States Patent
Feldchtein et al.

(10) Patent No.: US 7,426,036 B2
(45) Date of Patent: Sep. 16, 2008

(54) COMMON PATH FREQUENCY DOMAIN OPTICAL COHERENCE REFLECTOMETER AND COMMON PATH FREQUENCY DOMAIN OPTICAL COHERENCE TOMOGRAPHY DEVICE

(75) Inventors: Felix I. Feldchtein, Cleveland, OH (US); Grigory V. Gelikonov, Nizhny Novgorod (RU)

(73) Assignee: Imalux Corporation, Cleveland, CO (US)

( * ) Notice: Subject to any disclaimer, the term of this patent is extended or adjusted under 35 U.S.C. 154(b) by 247 days.

(21) Appl. No.: 11/456,414

(22) Filed: Jul. 10, 2006

(65) Prior Publication Data

US 2007/0008545 A1 Jan. 11, 2007

Related U.S. Application Data

(60) Provisional application No. 60/697,714, filed on Jul. 8, 2005.

(51) Int. Cl.
*G01B 9/02* (2006.01)
*G01B 11/02* (2006.01)
(52) U.S. Cl. ............ 356/479; 356/497
(58) Field of Classification Search ......... 356/477–479, 356/491, 492, 496, 497, 500
See application file for complete search history.

(56) References Cited

U.S. PATENT DOCUMENTS

| 5,268,741 | A | * | 12/1993 | Chou et al. | 356/479 |
|---|---|---|---|---|---|
| 5,956,355 | A | * | 9/1999 | Swanson et al. | 372/20 |
| 6,053,613 | A | * | 4/2000 | Wei et al. | 351/205 |
| 6,160,826 | A | * | 12/2000 | Swanson et al. | 372/20 |
| 6,501,551 | B1 | * | 12/2002 | Tearney et al. | 356/477 |
| 6,552,797 | B2 | * | 4/2003 | Swanson | 356/479 |
| 6,687,010 | B1 | * | 2/2004 | Horii et al. | 356/479 |
| 6,738,144 | B1 | * | 5/2004 | Dogariu | 356/479 |
| 7,280,221 | B2 | * | 10/2007 | Wei | 356/479 |
| 2003/0103212 | A1 | * | 6/2003 | Westphal et al. | 356/479 |

(Continued)

OTHER PUBLICATIONS

Kobayashi et al., "Optical Fiber Component Characterization by Hygh-Intensity and High-Spatial-Resolution Interferometric Optical-Time_Domain Reflectometer," Jun. 1991, IEEE Photonics Technology Letters, vol. 3, No. 6, pp. 564-566.*

(Continued)

*Primary Examiner*—Patrick Connolly
*Assistant Examiner*—Scott M Richey
(74) *Attorney, Agent, or Firm*—Renner, Otto, Boisselle & Sklar, LLP (57) ABSTRACT

Common path frequency domain optical coherence reflectometry/tomography devices with an additional interferometer are suggested. The additional interferometer offset is adjusted such, that it is ether less than the reference offset, or exceeds the distance from the reference reflector to the distal boundary of the longitudinal range of interest. This adjustment allows for relieving the requirements to the spectral resolution of the frequency domain optical coherence reflectometry/tomography engine and/or speed of the data acquisition and processing system, and eliminates depth ambiguity problems. The new topology allows for including a phase or frequency modulator in an arm of the additional interferometer improving the signal-to-noise ratio of the devices. The modulator is also capable of substantially eliminating mirror ambiguity, DC artifacts, and autocorrelation artifacts. The interference signal is produced either in the interferometer or inside of the optical fiber probe leading to the sample.

35 Claims, 4 Drawing Sheets

U.S. PATENT DOCUMENTS

2004/0239938 A1* 12/2004 Izatt .......................... 356/450
2004/0239943 A1* 12/2004 Izatt et al. ................... 356/479
2005/0140982 A1* 6/2005 Chen et al. .................. 356/479

OTHER PUBLICATIONS

Kobayashi et al., "Polarization-Independent Interferometric Optical-Time_Domain Reflectometer," May 1991, J. of Lightwave Tech., vol. 9, No. 5, pp. 623-628.*

Kobayashi et al., "High-spatial-resolution and high-sensitivity interferometric optical-time-domain reflectometer," 1991, SPIE, vol. 1474, pp. 278-284.*

Takada et al., "Rayleigh backscattering measurement of single-mode fibers by low coherence optical time-domain reflectometer with 14 micron spatial resolution," Jul. 8, 1991, Appl. Phys. Lett, 59 (2), pp. 143-145.*

Ozeki et al., "Polarization-mode dispersion measurement by an optical time-domain reflectometer with polarimetry assuming backscattering by randomly oriented nonspherical particles," Aug. 1, 2003, Optics Letters, vol. 28, No. 15, pp. 1293-1295.*

* cited by examiner

COMMON PATH FREQUENCY DOMAIN OPTICAL COHERENCE REFLECTOMETER AND COMMON PATH FREQUENCY DOMAIN OPTICAL COHERENCE TOMOGRAPHY DEVICE

CROSS-REFERENCE TO RELATED APPLICATIONS

This application is based on and claims priority to provisional U.S. patent application Ser. No. U.S. 60/697,714, which was filed on Jul. 8, 2005.

BACKGROUND OF THE INVENTION

The present invention relates to systems and methods for visualizing subsurface regions of samples, and more specifically, to a frequency domain optical coherence reflectometer and frequency domain optical coherence tomography (OCT) device that provides internal depth profiles and depth resolved images of samples.

Optical coherence reflectometry/tomography involves splitting an optical radiation to at least two portions, and directing one portion of the optical radiation toward a subject of investigation. The subject of investigation will be further referred to as a "sample", whereas the portion of optical radiation directed toward the sample will be further referred to as a "sample portion" of optical radiation. The sample portion of optical radiation is directed toward the sample by means of a delivering device, such as an optical probe. Another portion of the optical radiation, which will be further referred to as "reference portion", is used to provide heterodyne detection of the low intensity radiation, reflected or backscattered from the sample.

Typically, any optical coherence reflectometer or OCT device is specified by a longitudinal (in-depth) range of interest, whereas the longitudinal range of interest and the sample overlap, at least partially. The longitudinal range of interest includes a proximal boundary and a distal boundary, and in time domain systems is equivalent to the longitudinal scanning range. In traditional time domain optical coherence reflectometry at every moment only a small part of the sample portion of the optical radiation, reflected or backscattered from some point located inside the boundaries of the longitudinal range of interest is utilized. In-depth profiling of the sample is provided by introducing a variable optical path length difference for the sample and reference portions of the optical radiation.

A well known version of time domain optical coherence reflectometry and tomography is the "common path" version, also known as autocorrelator or Fizeau interferometer based OCR/OCT. In this version, the reference and sample portions of the optical radiation do not travel along separate optical paths. Instead, a reference reflection is created in the sample optical path by introducing an optical inhomogenuity in the distal part of the delivering device, the inhomogenuity serving as a reference reflector. Resulting from that, the reference and sample portions of the optical radiation experience an axial shift only. The distance between the reference reflector and the front boundary of the longitudinal range of interest will be considered here as "reference offset". The entire combination of the sample portion of the optical radiation and axially shifted reference portion is combined with the replica of the same combination, shifted axially, so the reference portion of one replica has a time of flight (or optical path length) matching that of the sample portion of another replica. These portions interfere in a very similar way to the traditional "separate path" time domain optical coherence reflectometry/tomography embodiments. The interference signal is formed by a secondary interferometer, the two arms of which have an optical length difference ("interferometer offset") equal to the reference offset. By scanning an optical delay between the two replicas, a time profile of the interference signal is obtained, which represents the in-depth profile of the coherent part of the reflected sample optical radiation. The later is substantially equivalent to the profile obtained in traditional separate path embodiments.

Common path time domain reflectometry/tomography has a lot of intrinsic advantages over separate path time domain reflectometry/tomography. These advantages are based on the fact that reference and sample portions of the optical radiation propagate in the same optical path and therefore experience substantially identical delay, polarization distortions, optical dispersion broadening, and the like. Therefore, the interference fringes are insensitive to the majority of the probe properties, including the optical fiber probe length, dispersion properties and polarization mismatch. In separate path time domain reflectometry/tomography, the length and dispersion of the sampling arm should be closely matched with the reference arm and the polarization mismatch should be prevented (using PM fiber or other means) or compensated (using polarization diversity receiver or other means).

The optical spectrum of the combined reference and sample portions of the optical radiation, both in the separate path and the common path reflectometry and OCT designs has all necessary information about the in-depth coherent reflection profile by including a component that is Fourier conjugate of the in-depth profile of the sample. Thus, the profile is capable of being extracted from Fourier transformation of the optical spectrum of the combined optical radiation.

Fourier transformation of the optical spectrum of the reference and sample optical radiation combination is actually well known and has been utilized in frequency domain optical coherence reflectometry and tomography (also known as spectral domain and Fourier domain) since 1995. In frequency domain optical coherence reflectometry the reference and sample portions of the optical radiation have a substantially similar optical path. The optical spectrum of the combined optical radiation can be registered using parallel means (such as a spectrograph) or sequential scanning means using a swept frequency optical source.

However, it took several years for the scientific community to realize that frequency domain optical coherence reflectometry/tomography has a fundamental, major advantage in signal-to-noise ratio (SNR) over traditional time-domain reflectometry/tomography. The frequency domain reflectometry/tomography SNR advantage can be explained by a simultaneous use of light coming back from all in-depth pixels, whereas in time domain reflectometry/tomography only light from one in-depth pixel is used at a time and all the rest is wasted. Therefore, the SNR for frequency domain reflectometry/tomography is capable of being improved by a factor equal to the number of in-depth pixels (which for a system with moderate in-depth resolution of 15 µm and scanning depth of 2 mm will be a factor of 133). It should be also noted that this advantage increases with improving in-depth resolution for the same depth, reaching a factor of 1000 for 2 µm resolution.

Common path frequency domain optical coherence reflectometry and tomography are well known in the art. However, previously known devices typically employ an optical layout where reference reflection occurs in the vicinity of the sample. In these devices the combination of reference and sample reflection is directly spectrally analyzed without any additional optical processing, such as using an additional interferometer. This approach works very well if stable reference reflection can be obtained from a point axially close to the sample. Unfortunately, in many situations, and in particular, in a probe design for medical application it is very difficult or even impossible to obtain reference reflection from the vicinity of the sample and instead, reference reflection can only be obtain from a point located far from the sample.

A limitation to such common path frequency domain OCR/OCT systems without a secondary interferometer is the great value of required spectral resolution of the frequency domain OCR/OCT processing engine. This limitation becomes especially important in medical applications. The problem is that even for miniature optical fiber endoscopic probes known in the art that use the optical fiber tip of the optical fiber probe as a reference element, the reference offset could be as big as 10 mm, since the optical fiber probe inevitably includes a lens system in its distal part. This distance may be greater if a bigger probe with a larger field of view is required, such as for laparoscopy. It is known that the larger the in-depth distance is between the most remote points involved in the optical interference (which is the reference offset plus intended depth range), the finer the spectral resolution of the system should be, in order to resolve the highest frequency spectral fringes.

The later can be illustrated referring to the spectrum of two pairs of pulses with different time separation. Each pair of pulses (for OCR/OCT corresponding to a pair of reflecting surfaces separated in depth) produces interference fringes in the spectrum. The frequency of spectral fringes increases accordingly with increasing of the delay between pulses. To restore the in-depth profile, the spectral resolution of the frequency domain OCR/OCT engine should be sufficient to resolve the most frequent fringes in the optical spectrum. In spatial-temporal terminology, the effective coherence length should be sufficient to provide interference between the most distant points. Therefore, a large reference offset creates unnecessary high spectral resolution requirements for the spectrometer or unnecessary strict instantaneous line width requirements for the tunable source. It also puts an additional burden on the data acquisition and real time signal processing system, where a several times increase of data flow is required for the same image acquisition rate. Additionally, the system design would require substantial changes if another probe with different reference offset is needed. All of the described is capable of making questionable the advantage of using common path topology in a frequency domain OCR/OCT system.

One solution would be to add an additional interferometer in the manner known for time domain OCT/OCR systems. Unfortunately, applying frequency domain registration to earlier separate path OCR/OCT systems creates a serious problem—the "depth ambiguity problem" (also referred to as mirror artifact or depth degeneracy). The problem is well known and is associated with Fourier transformation's inability to differentiate between positive and negative depth coordinates in a case of the optical path difference for the interfering reference and sample portions of the optical radiation being reduced to zero. The same problem would arise for a common path frequency domain OCR/OCT system utilizing a secondary interferometer since in a system of this type, as discussed above, the interference signal is formed by reducing to zero the optical path difference for the interfering reference and sample portions of the two replicas of the optical radiation. There are several ways known to deal with the depth degeneracy problem, all of them being cost consuming and rather complicated for being used in a medical device.

SUMMARY OF THE INVENTION

Improved optical coherence reflectometry and optical coherence tomography devices have been developed that utilize the advantages of a common path optical interferometer design together with the advantages of frequency domain registration of the optical spectrum of the combined reference and sample portions of the optical radiation, overcoming at the same time limitations of both approaches.

According to one aspect of the present invention, a common path frequency domain optical coherence reflectometer is provided that includes a source of an optical radiation, a directional element, and a delivering device. The delivering device is adapted to form and deliver an optical radiation beam to a sample. The delivering device has a proximal part and a distal part, which distal part includes a reference reflector. The common path frequency domain optical coherence reflectometer also includes an optical unit, optically coupled with the proximal part of the delivering device through the directional element, and an optical element for producing a combination optical radiation by combining an optical radiation returning from the sample with a reference optical radiation reflected from the reference reflector. Also included in the common path frequency domain optical coherence reflectometer is a frequency domain optoelectronic registering unit adapted to register the combination optical radiation. The frequency domain optoelectronic registering unit includes a data processing and displaying unit. The optical unit of the frequency domain optical coherence reflectometer includes an optical element for splitting an incoming optical radiation into two portions, and at least two optical paths adapted for the respective portions of the optical radiation to propagate therethrough. The at least two optical paths of the optical unit have an optical path length difference.

The common path frequency domain optical coherence reflectometer of the invention is further specified by a longitudinal range of interest, including a proximal boundary and a distal boundary, and at least partially overlapping with the sample. The common path frequency domain optical coherence reflectometer of the invention has an optical path length difference of a first value for the optical radiation beam propagating to the reference reflector and to the proximal boundary of the longitudinal range of interest, has an optical path length difference of a second value for the optical radiation beam propagating to the reference reflector and to the distal boundary of the longitudinal range of interest.

In a preferred embodiment, the value of the optical path length difference for the two portions of the optical radiation propagating in the optical unit is one of the following: less than the first value, and exceeds the second value.

In another embodiment the value of the optical path length difference for the two portions of the optical radiation propagating in the optical unit lies between the first and second values. In this embodiment, at least one of the optical paths of the optical unit further includes a device adapted for substantially eliminating at least one of mirror ambiguity, DC artifacts, and autocorrelation artifacts.

In another preferred embodiment the optical unit is in optical communication with the source of optical radiation through the directional element. In this embodiment, the reference reflector serves as the optical element for producing the combination optical radiation. Preferably, the optical unit is an optical interferometer, the at least two optical paths of the optical unit being the arms of the optical interferometer. According to one aspect of the invention, each arm of the optical interferometer includes a Faraday mirror at its end. According to another aspect of the invention, at least one of the arms of the optical interferometer includes a regular mirror at its end, and at least one arms of the optical interferometer includes a polarization controller.

In an alternative embodiment, the delivering device is in optical communication with the source of optical radiation through the directional element. In this embodiment, the optical unit further includes the optical element for producing the combination optical radiation. According to one aspect of the invention, the optical element of the optical unit for splitting an incoming optical radiation into two portions of the optical radiation further serves as the optical element for producing the combination optical radiation. According to another aspect of the invention, the optical unit is an optical interferometer, the at least two optical paths of the optical unit being the arms of the optical interferometer. The arms of the optical interferometer each include a Faraday mirror at its end.

In a further embodiment of the present invention, at least one of the optical paths of the optical unit further includes a device adapted for substantially eliminating at least one of mirror ambiguity, DC artifacts, and autocorrelation artifacts.

In a still further embodiment, at least one of the optical paths of the optical unit further includes means adapted for improving a signal-to-noise ratio of the common path frequency domain optical coherence reflectometer. The means adapted for improving the signal-to-noise ratio includes one of a phase modulator, and a frequency modulator.

In a still further embodiment, at least one of the optical paths of the optical unit further includes a device adapted for substantially eliminating at least one of mirror ambiguity, DC artifacts, and autocorrelation artifacts, and includes means adapted for improving a signal-to-noise ratio of the common path frequency domain optical coherence reflectometer. The means adapted for improving the signal-to-noise ratio includes one of a phase modulator, and a frequency modulator.

In another preferred embodiment, the optical device adapted for substantially eliminating at least one of mirror ambiguity, DC artifacts, autocorrelation artifacts, is further adapted for improving the signal-to-noise ratio. Preferably, the means adapted for substantially eliminating at least one of mirror ambiguity, DC artifacts, autocorrelation artifacts, and improving the signal-to-noise ratio includes one of a phase modulator, and a frequency modulator.

According to one aspect of the present invention, the source of optical radiation is made tunable. In this embodiment, the frequency domain optoelectronic registering unit includes at least one photodetector connected with the data processing and displaying unit.

According to one aspect of the present invention, the source of optical radiation is a low-coherence source of optical radiation. In this embodiment, the frequency domain optoelectronic registering unit includes a spectrometer connected with the data processing and displaying unit.

In a preferred embodiment the delivering device is an optical fiber probe. Preferably, the tip of the optical fiber included in the probe, serves as the reference reflector.

In an alternative embodiment, the common path frequency domain optical coherence reflectometer of the present invention further including means for changing relative positions of the optical radiation beam being delivered to the sample, and the sample. In this embodiment the common path frequency domain optical coherence reflectometer is part of a common path frequency domain device for optical coherence tomography.

In one embodiment, the source of optical radiation is made tunable. In this embodiment, the frequency domain optoelectronic registering unit includes at least one photodetector connected with the data processing and displaying unit.

In another embodiment, the source of optical radiation is a low-coherence source of optical radiation. In this embodiment, the frequency domain optoelectronic registering unit includes a spectrometer connected with the data processing and displaying unit.

In accordance with another aspect of the present invention, a common path frequency domain optical coherence tomography device is provided that includes a source of optical radiation, a directional element, and an optical fiber probe adapted to form and deliver an optical radiation beam to a sample. The optical fiber probe includes an optical fiber. A tip of the optical fiber serves as a reference reflector. The common path frequency domain optical coherence tomography device also includes an optical interferometer, which is in optical communication with the optical fiber probe through the directional element. Also included in the common path frequency domain optical coherence tomography device is an optical element for producing a combination optical radiation by combining an optical radiation returning from the sample with a reference optical radiation reflected from the tip of the optical fiber of the optical fiber probe. Also included in the common path frequency domain optical coherence tomography device of the present invention is means for changing relative positions of the optical radiation beam being delivered to the sample, and the sample, and a frequency domain optoelectronic registering unit. The frequency domain optoelectronic registering unit is adapted to register the combination optical radiation and includes a data processing and displaying unit. The optical interferometer includes an optical element for splitting an incoming optical radiation into two portions, and at least two arms adapted for the respective portions of the optical radiation to propagate therethrough. The at least two arms of the optical interferometer have an optical path length difference and each include a mirror at their end.

In one embodiment, at least one arm of the optical interferometer includes an optical device adapted for substantially eliminating at least one of mirror ambiguity, DC artifacts, and autocorrelation artifacts, and adapted for improving a signal-to-noise ratio of the common path frequency domain optical coherence tomography device. Preferably, the optical device adapted for substantially eliminating at least one of mirror ambiguity, DC artifacts, autocorrelation artifacts, and adapted for improving the signal-to-noise ratio includes one of a phase modulator, and a frequency modulator.

The common path frequency domain optical coherence tomography device of the present invention is specified by a longitudinal range of interest including a proximal boundary and a distal boundary, and at least partially overlapping with the sample. The common path frequency domain optical coherence tomography device has an optical path length difference of a first value for the optical radiation beam propagating to the tip of the optical fiber of the optical fiber probe and to the proximal boundary of the longitudinal range of interest, and has an optical path length difference of a second value for the optical radiation beam propagating to the tip of the optical fiber of the optical fiber probe and to the distal boundary of the longitudinal range of interest. Preferably, the value of the optical path length difference of the at least two arms of the optical interferometer is one of the following: less than the first value, and exceeds the second value.

In a preferred embodiment, the optical interferometer is in optical communication with the source of optical radiation through the directional element. In this embodiment, the tip of the optical fiber probe serves as the optical element for producing the combination optical radiation. In accordance with one aspect of the invention, each arm of the optical interferometer includes a Faraday mirror. In accordance with another aspect of the invention, at least one arm of the optical interferometer includes a regular mirror, and wherein at least one arm of the optical interferometer includes a polarization controller.

In another preferred embodiment, the optical fiber probe is in optical communication with the source of optical radiation through the directional element. In this embodiment, the optical interferometer further includes the optical element for producing the combination optical radiation, wherein each arm of the optical interferometer includes a Faraday mirror.

In another preferred embodiment of the present invention, the optical element of the optical interferometer for splitting an incoming optical radiation into two portions of the optical radiation further serves as the optical element for producing the combination optical radiation.

In accordance with one aspect of the present invention, the source of optical radiation is made tunable. In this embodiment the frequency domain optoelectronic registering unit includes at least one photodetector connected with the data processing and displaying unit.

In accordance with another aspect of the present invention, the source of optical radiation is a low-coherence source of optical radiation. In this embodiment the frequency domain optoelectronic registering unit includes a spectrometer connected with the data processing and displaying unit.

Thus, having the interferometer offset differ from the reference offset in the common path frequency domain optical coherence reflectometry and optical coherence tomography devices of the present invention allows for relieving the requirements to the spectral resolution of the FD OCT engine and/or data acquisition and processing system, and eliminates depth ambiguity problems. The topology of the devices of the subject invention allows for including a phase or frequency modulator in an arm of the interferometer. The later provides improving of a signal-to-noise ratio (SNR) of the common path frequency domain optical coherence reflectometer and of the optical coherence tomography device. The frequency modulator at the same time is capable of substantially eliminating mirror ambiguity, DC artifacts, and autocorrelation artifacts. Still other advantages, aspects and features of the subject invention will become readily apparent to those skilled in the art from the following description wherein there are shown and described preferred embodiments of the subject invention, simply by way of illustration of the best modes best suited to carry out the subject invention. The topology of the devices of the subject invention allows also for including a regular mirror in at least one arm of the optical interferometer, and including a polarization controller in at least one arm of the optical interferometer. The later results in a capability of the device to produce cross-polarization OCT images, as well as producing traditional parallel polarization OCT images. As it will be realized, the subject invention is capable of other different embodiments and its several details are capable of modifications in various obvious aspects all without departing from the scope of the subject invention. Accordingly, the drawings and descriptions will be regarded as illustrative in nature and not as restrictive.

BRIEF DESCRIPTION OF DRAWINGS

For a more complete understanding of the present invention and the advantages thereof, reference is now made to the following description taken in conjunction with the accompanying drawings, in which.

DETAILED DESCRIPTION OF THE INVENTION

The subject application is directed to systems and methods for visualizing subsurface regions of samples, and more specifically, to a frequency domain optical coherence reflectometer and frequency domain optical coherence tomography device that provides internal depth profiles and depth images of samples. Modifications of the common path frequency domain optical coherence reflectometer are illustrated by means of examples of optical fiber devices being part of an apparatus for optical coherence tomography, although it is evident that they may be implemented with the use of bulk optic elements, and may be used as independent devices. The optical fiber implementation is preferable for use in medical applications, especially in endoscopy, where flexibility of the optical fiber provides convenient access to different tissues and organs, including internal organs via an endoscope. However, the whole device, or any part of it, can be implemented using traditional bulk optics: mirrors, prisms etc.

Figure 1:
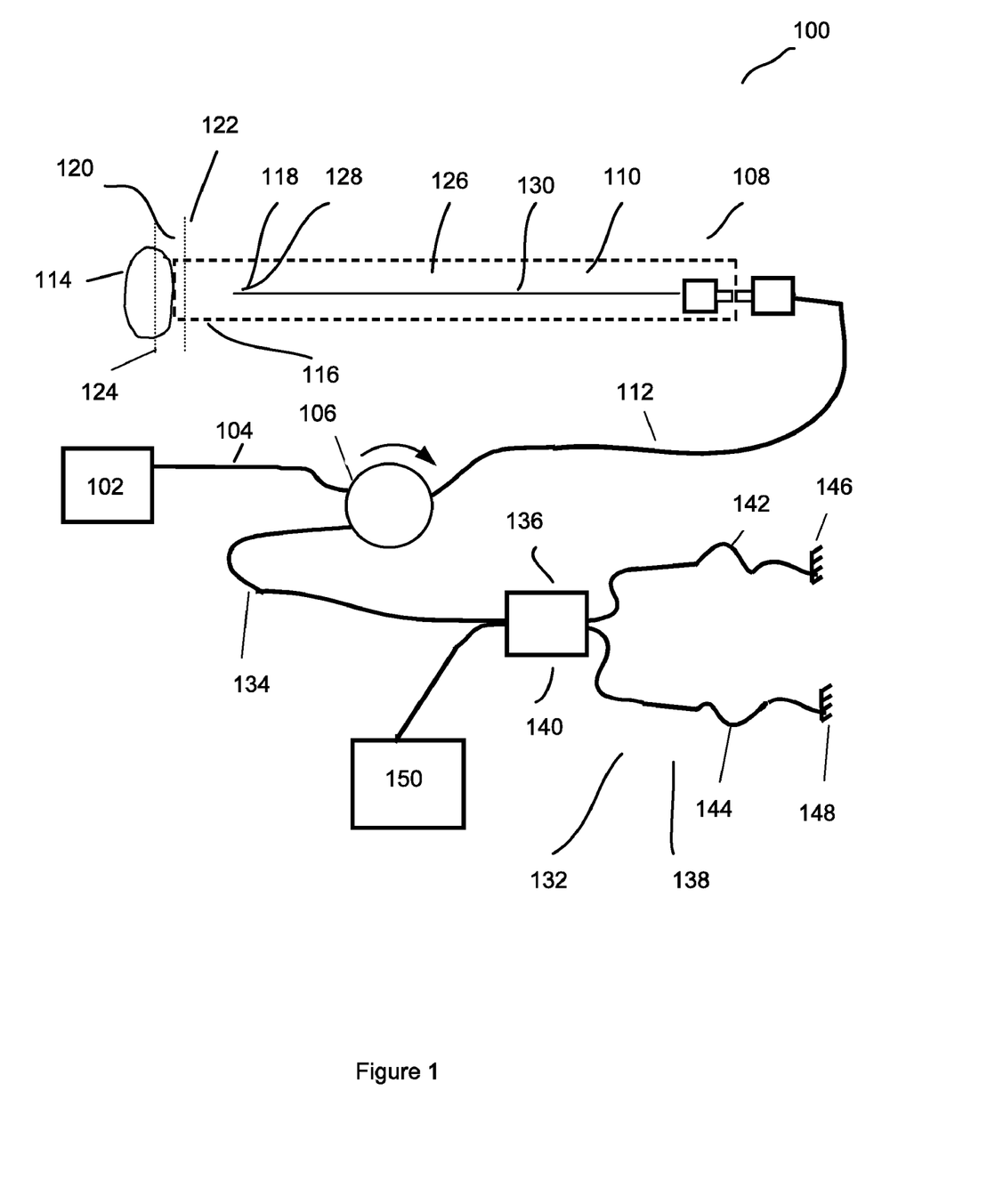
FIG. 1 is a block diagram of one preferred embodiment of the common path frequency domain optical coherence reflectometer of the invention.

Turning now to FIG. 1, there is shown a block diagram of an embodiment of the common path frequency domain optical coherence reflectometer 100. Referring to operation of the common path frequency domain optical coherence reflectometer 100 illustrated in FIG. 1, an optical radiation from a source 102 through an optical fiber 104 is directed to a directional element 106 that couples the source 102 with a proximal part 108 of a delivering device 110 through an optical fiber 112. In a preferred embodiment, the source 102 operates in the visible or near IR range. The source 102 is arranged, for example, and without limitation, as a semiconductor superluminescent diode, doped-fiber amplified spontaneous emission superlum, solid state and fiberoptic femtosecond laser. A skilled artisan will appreciate that the directional element 106 is implemented, for example, and without limitation, as a circulator or a directional coupler. The delivering device 110 is adapted to form and deliver an optical radiation beam to a sample 114 and, as will be recognized by those skilled in the art, includes a lens system (not shown) in its distal part 116. The distal part 116 of the delivering device 110 includes a reference reflector 118. The optical coherence reflectometer of FIG. 1 is specified by a longitudinal range of interest 120, in which the study of the sample 114 is performed. The longitudinal range of interest 120 overlaps, at least partially, with the sample 114 and includes a proximal boundary 122 and a distal boundary 124. For performing optical measurements, the delivering device 110 is placed at a predetermined position with respect to the sample 114. Depending basically on the tasks performed, the delivering device 110 is placed in the vicinity of the sample 114, in contact with the sample 114, or at a predetermined distance from the sample 114. In all cases, there is a distance between the reference reflector 118 and the proximal boundary 122 of the longitudinal range of interest 120, which is specified by an optical path length of a first value (reference offset). The distance between the reference reflector 118 and the distal boundary 124 of the longitudinal range of interest 120, will be specified here by an optical path length of a second value.

In a preferred embodiment illustrated in FIG. 1, the delivering device 110 is made as an optical fiber probe 126 with a tip 128 of an optical fiber 130 of the optical fiber probe 126 serving as the reference reflector 118. Hence, in the preferred embodiment the tip 128 of the optical fiber 130 is positioned at a distance having a first optical length value from the proximal boundary 122 of the longitudinal range of interest 120 (reference offset), or, in other words, having a second optical length value from the distal boundary 124 of the longitudinal range of interest 120.

Thus, part of the optical radiation beam from the source 102 is delivered to the sample 114 and is reflected or backscattered from it (the sample portion), i.e., from some point located inside the boundaries 122, 124 of the longitudinal range of interest 120. Another part of the optical radiation that enters the optical fiber probe 126 does not reach the sample 114, but is instead reflected at the tip 128 of optical fiber 130 of the optical fiber probe 126, at some distance from the sample 114 (the reference portion). The optical radiation returning from the optical fiber probe 126 is a combination of the reference and sample portions of the optical radiation, shifted axially. This combination is directed to an optical unit 132 through the optical fiber 112, the directional element 106, and an optical fiber 134. The optical unit 132 includes an element 136 for splitting the optical radiation incoming from the delivering device 110 into two portions of the optical radiation and recombining the two portions of the optical radiation. Thus, as will be appreciated by those skilled in the art, in the embodiment illustrated in FIG. 1, the optical element for producing a combination optical radiation by combining an optical radiation returning from the sample with a reference optical radiation reflected from the reference reflector is included in the optical unit 132. The topology and design of the optical unit 132 suitably varies. For illustration purposes the optical unit 132 is depicted in FIG. 1 as an all-fiber Michelson interferometer 138. A skilled artisan will appreciate that the optical unit 132 is capable of being implemented as any other optical interferometer known in the art including without limitation, a Mach-Zander interferometer. In the Michelson interferometer 138 of FIG. 1, the element 136 for splitting and recombining the optical radiation is implemented, for example, and without limitation, as a 3 dB directional coupler 140. The Michelson interferometer 138 includes a first arm 142 and a second arm 144. The first arm 142 of the Michelson interferometer 138 includes a first Faraday mirror 146 at its end, and the second arm 144 of the Michelson interferometer 138 includes a second Faraday mirror 148 at its end.

The combined optical radiation, returning from the optical fiber probe 126 is split by the directional coupler 140 into two portions of optical radiation, each portion comprising a combination of the reference and sample portions of the optical radiation, shifted axially. The directional coupler 140 directs one combination portion along the first arm 142 and directs the other combination portion along the second arm 144 of the Michelson interferometer 138.

The optical unit 132 has an optical path length difference for the two portions of the optical radiation propagating therethrough. In one preferred embodiment, the value of the optical path length difference for the two portions of the optical radiation in the optical unit 132 is less than the first optical length value for the distance between the optical reflector 118 and the proximal boundary 122 of the longitudinal range of interest 120. In another preferred embodiment, the value of the optical path length difference for the two portions of the optical radiation in the optical unit 132 exceeds the second optical length value for the distance between the optical reflector 118 and the distal boundary 124 of the longitudinal range of interest 120.

With respect to FIG. 1 with the Michelson interferometer 138 used as the optical unit 132, the Michelson interferometer 138 is characterized by an optical path length difference between the first arm 142 and the second arm 144. In one preferred embodiment, the value of this optical path length difference (interferometer offset) is less than the first optical path length value between the tip 128 of the optical fiber 130 and the proximal boundary 122 of the longitudinal range of interest 120 (reference offset). In another preferred embodiment, the value of this optical path length difference (interferometer offset) exceeds the second optical path length value between the tip 128 of the optical fiber 130 and the distal boundary 124 of the longitudinal range of interest 120. The interferometer offset is adjusted in the process of assembling the interferometer 138. As will be recognized by those skilled in the art, the value of the interferometer offset being less than the reference offset, or exceeding the distance from the reference reflector 118 to the distal boundary 124 of the longitudinal range of interest 120, nonetheless stays in the vicinity of the value of the reference offset.

The two combined portions after being reflected by respective Faraday mirrors 146, 148, are combined by the directional coupler 140, thereby a combination optical radiation is produced by the directional coupler 140. The two portions interfere in a very similar way to the traditional separate path optical coherence reflectometer. The combination optical radiation from the directional coupler 140 is registered by a frequency domain optoelectronic registering unit 150 including a data processing and displaying unit (not shown in the drawing), and optically coupled with the optical unit 132 (interferometer 138). The optical spectrum of the combination optical radiation has all necessary information about the in-depth coherent reflection profile by including a component that is Fourier conjugate of the in-depth profile of the sample. Thus, the profile is extracted from Fourier transformation of the optical spectrum of the combined optical radiation by the data processing and displaying unit of the frequency domain optoelectronic registering unit 150. No depth ambiguity problem arises since the optical path difference for the interfering reference and any part of sample portion belonging to the longitudinal range of interest 120 for the two replicas of the optical radiation is not reduced to zero.

In one embodiment, the source 102 of optical radiation is narrowband and tunable, whereas the frequency domain optoelectronic registering unit 150 includes at least one photodetector connected with the data processing and displaying unit (not shown in FIG. 1). In another embodiment the source 102 is broadband and implemented as a low-coherence source of optical radiation. In this embodiment a spectrometer instead of a single photodiode is used in the frequency domain optoelectronic registering unit 150, therefore parallel registration is performed instead of sequential. Those skilled in the art will appreciate that no optical path difference scanning is necessary in these embodiments, and therefore, no optical path difference scanning is performed.

A slow delay line suitably adapted to control the axial position of the observation zone is capable of being introduced in any of the arms of the optical unit 132 (not shown in the drawing).

In another embodiment, the value of the optical path length difference for the two portions of the optical radiation in the optical unit 132 (optical path length difference between the arms 142, 144 of the interferometer 138) lies between the first and second optical path length values. In this case at least one of the optical paths for the two portions of the optical radiation of the optical unit 132 (one of the arms 142, 144 of the optical interferometer 138) includes a device for eliminating mirror ambiguity, DC artifacts, and autocorrelation artifacts. One skilled in the art will recognize that the device for eliminating mirror ambiguity, DC artifacts, and autocorrelation artifacts is suitably implemented in accordance with well known prior art.

In another preferred embodiment the common path frequency domain optical coherence reflectometer is part of a common path frequency domain device for optical coherence tomography and includes means adapted for changing the relative positions of the optical radiation beam being delivered to the sample 114, and the sample 114 (not shown in FIG. 1).

In another embodiment, at least one arm of the interferometer 138 also includes means for improving the SNR of the common path frequency domain reflectometer or of the common path frequency domain optical coherence tomography device (not shown in the drawing). A skilled artisan will recognize that this means suitably includes a phase modulator or a frequency modulator. In a preferred embodiment, the phase modulator or the frequency modulator included in one of the arms of the optical interferometer 138 substantially eliminates mirror ambiguity, DC artifacts, and autocorrelation artifacts, and improves the SNR of the devices of the subject invention, as well. The topology of the devices of the subject invention allows also for including a dispersion compensation unit in an arm of the optical interferometer 138 (not shown) to compensate a dispersion mismatch in the sample and reference optical paths.

Figure 2:
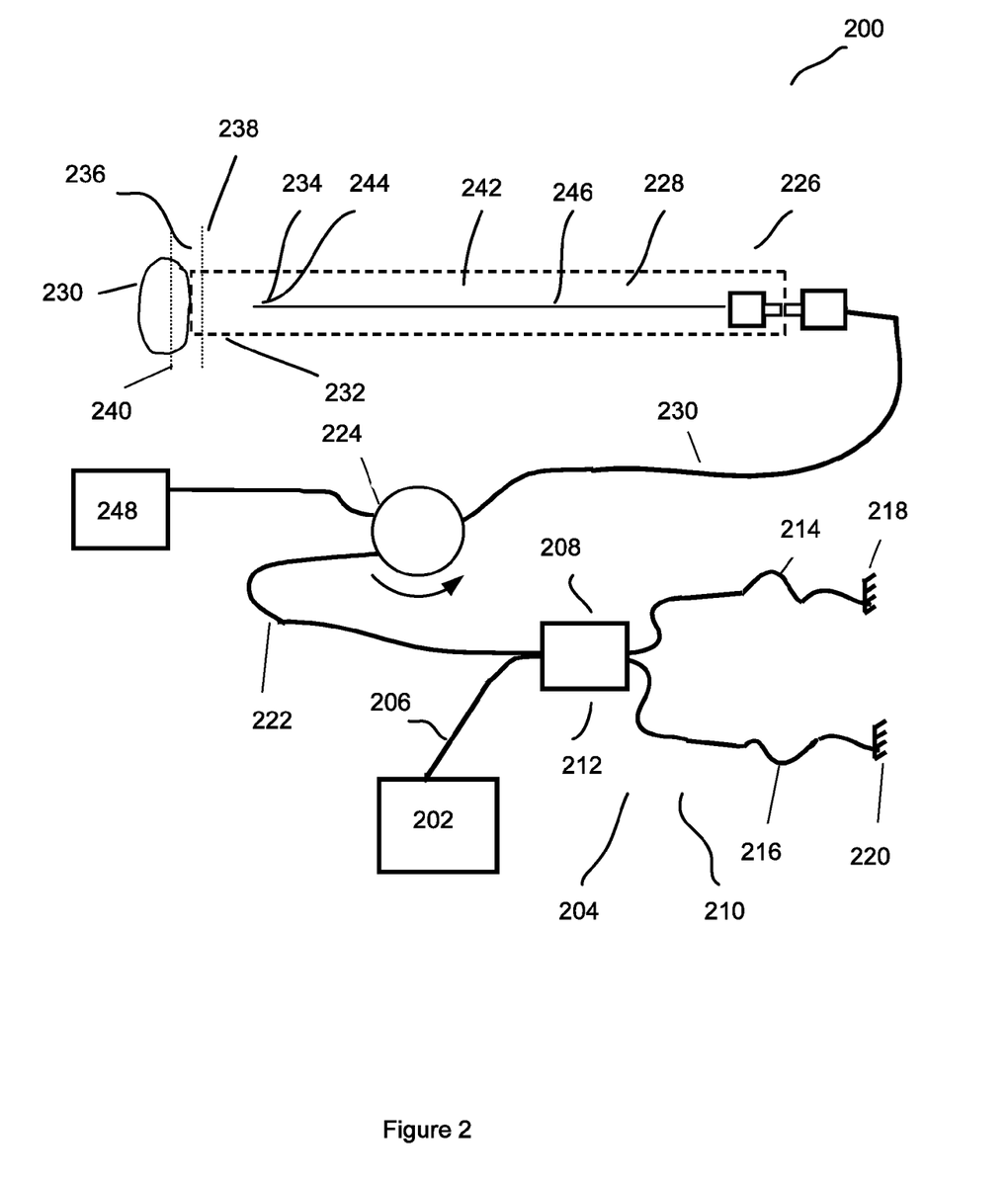
FIG. 2 is a schematic diagram of another preferred embodiment of the common path frequency domain optical coherence reflectometer of the invention.

Referring now to FIG. 2, there is shown a block diagram of another embodiment of the common path frequency domain optical coherence reflectometer 200. Referring to operation of the common path frequency domain optical coherence reflectometer 200 illustrated in FIG. 2, an optical radiation from a source 202 is directed to an optical unit 204 through an optical fiber 206. A skilled artisan will recognize that the source 202 is analogous to the source 102 of the device depicted in FIG. 1. The optical unit 204 includes an element 208 for splitting the optical radiation incoming from the source 202 into two portions of the optical radiation. The topology and design of the optical unit 204 suitably varies. For illustration purposes the optical unit 204 is depicted in FIG. 2 as an all-fiber Michelson interferometer 210. A skilled artisan will appreciate that the optical unit 204 is capable of being implemented as any other optical interferometer known in the art including without limitation, a Mach-Zander interferometer. In the Michelson interferometer 210 of FIG. 2, the element 208 for splitting and recombining the optical radiation is implemented, for example, and without limitation, as a 3 dB directional coupler 212. The Michelson interferometer 210 includes a first arm 214 and a second arm 216. The first arm 214 of the Michelson interferometer 210 includes a first mirror 218 at its end, and the second arm 216 of the Michelson interferometer 210 includes a second mirror 220 at its end. The directional coupler 212 directs one portion of the optical radiation incoming from the source 202 along the first arm 214 and directs the other portion of the optical radiation incoming from the source 202 along the second arm 216 of the Michelson interferometer 210.

The optical unit 204 has an optical path length difference for the two portions of the optical radiation propagating therethrough. With respect to FIG. 2 with the Michelson interferometer 210 used as the optical unit 204, the Michelson interferometer 210 is characterized by an optical path length difference between the first arm 214 and the second arm 216, which is referred to as an interferometer offset. The two portions of optical radiation after being reflected from respective mirrors 218, 220 enter the directional coupler 212. The directional coupler 212 directs the two portions of optical radiation into an optical fiber 222. Next, the two portions of optical radiation, being shifted due the optical path length difference between the first arm 214 and the second arm 216 of the interferometer 210, enter a directional element 224. A skilled artisan will appreciate that the directional element 224 is suitably implemented analogous to the directional element 106 of the device illustrated in FIG. 1. The directional element 224 couples the optical unit 204 (the optical interferometer 210) with a proximal part 226 of a delivering device 228 through an optical fiber 230. The delivering device 228 analogous to delivering device 108 of the common path frequency domain optical coherence reflectometer illustrated in FIG. 1, is adapted to form and deliver an optical radiation beam to a sample 230. As will be recognized by those skilled in the art, the delivering device 228 includes a lens system (not shown) in its distal part 232. The distal part 232 of the delivering device 228 includes a reference reflector 234. The optical coherence reflectometer of FIG. 2 is specified by a longitudinal range of interest 236, in which the study of the sample 230 is performed. The longitudinal range of interest 236 overlaps, at least partially, with the sample 230 and includes a proximal boundary 238 and a distal boundary 240. For performing optical measurements, the delivering device 228 is placed at a predetermined position with respect to the sample 230. Analogous to the device depicted in FIG. 1, a distance between the reference reflector 234 and the proximal boundary 238 of the longitudinal range of interest 236 is specified by an optical path length of a first value (reference offset), whereas a distance between the reference reflector 234 and the distal boundary 240 of the longitudinal range of interest 236, is specified by an optical path length of a second value.

In a preferred embodiment illustrated in FIG. 2, the delivering device 228 is made as an optical fiber probe 242 with a tip 244 of an optical fiber 246 of the optical fiber probe 242 serving as the reference reflector 234. Hence, in the preferred embodiment the tip 244 of the optical fiber 246 is positioned at a distance having a first optical length value from the proximal boundary 238 of the longitudinal range of interest 236 (reference offset), or, in other words, having a second optical length value from the distal boundary 240 of the longitudinal range of interest 236.

Returning now to the optical unit 204, the value of the optical path length difference for the two portions of the optical radiation propagating therethrough, in one preferred embodiment, is less than the first optical length value for the distance between the optical reflector 234 and the proximal boundary 238 of the longitudinal range of interest 236. In another preferred embodiment, the value of the optical path length difference for the two portions of the optical radiation in the optical unit 204 exceeds the second optical length value for the distance between the optical reflector 234 and the distal boundary 240 of the longitudinal range of interest 236. With respect to FIG. 2 with the Michelson interferometer 210 used as the optical unit 204, the Michelson interferometer 210 is characterized by an optical path length difference between the first arm 214 and the second arm 216. In one preferred embodiment, the value of this optical path length difference (interferometer offset) is less than the first optical path length value between the tip 244 of the optical fiber 246 and the proximal boundary 238 of the longitudinal range of interest 236 (reference offset). In another preferred embodiment, the value of this optical path length difference (interferometer offset) exceeds the second optical path length value between the tip 244 of the optical fiber 246 and the distal boundary 240 of the longitudinal range of interest 236. The interferometer offset is adjusted in the process of assembling the interferometer 210. As will be recognized by those skilled in the art, the value of the offset of the interferometer 210 being less than the reference offset, or exceeding the distance from the reference reflector 234 to the distal boundary 240 of the longitudinal range of interest 236, nonetheless stays in the vicinity of the value of the reference offset.

Thus, one part of the each portion of the optical radiation beam is delivered to the sample 230 and is reflected or backscattered from it (the sample portion), i.e., from some point located inside the boundaries 238, 240 of the longitudinal range of interest 236. Another part of the each portion of the optical radiation that enters the optical fiber probe 242 does not reach the sample 230, but is instead reflected at the tip 244 of optical fiber 246 of the optical fiber probe 242, at some distance from the sample 230 (the reference portion). Those skilled in the art will appreciate that due to the mentioned above relationship between the reference offset and the interferometer offset, the tip 244 of optical fiber 246 produces a combination optical radiation in a manner similar to that of the directional coupler 140 in the common path frequency domain optical coherence reflectometer illustrated in FIG. 1. The tip 244 of optical fiber 246 combines an optical radiation returning from the sample 230 of one portion of optical radiation with a reference optical radiation being reflected from the tip 244 (reference reflector 234) of the other portion.

The combination optical radiation returning from the delivering device 228 (optical fiber probe 242) is directed to a frequency domain optoelectronic registering unit 248 including a data processing and displaying unit (not shown in the drawing) by the directional element 224. The combination optical radiation is registered by the frequency domain optoelectronic registering unit 248. Analogous to that described with reference to the common path frequency domain optical coherence reflectometer depicted in FIG. 1, the optical spectrum of the combination optical radiation registered by the frequency domain optoelectronic registering unit 248, has all necessary information about the in-depth coherent reflection profile by including a component that is Fourier conjugate of the in-depth profile of the sample. Thus, the profile is extracted from Fourier transformation of the optical spectrum of the combined optical radiation by the data processing and displaying unit of the frequency domain optoelectronic registering unit 248. No depth ambiguity problem arises since the optical path difference for the interfering reference and any part of sample portion belonging to the longitudinal range of interest of the two replicas of the optical radiation is not reduced to zero.

In one preferred embodiment, the mirrors 218, 220 of the interferometer 210 are implemented as Faraday mirrors to compensate for polarization distortions occurring in the optical fiber elements. In another preferred embodiment, the mirrors 218, 220 of the interferometer 210 are implemented as regular mirrors, whereas at least one arm 214, 216 of the interferometer 210 includes a polarization controller (not shown in the drawing). This approach is applicable only for the type of optical layout illustrated in FIG. 2, where the optical radiation passes the interferometer 210 before entering the optical fiber probe 242. In this case the polarization controller is capable of being aligned just the once because the polarization of the optical radiation entering the interferometer 210 does not change as the optical fiber 246 of the probe 242 is bent. The manner in which the polarization controller is aligned depends on the type of images chosen for being registered. In accordance with one aspect of the invention, the polarization controller is aligned such that the two portions of the optical radiation are parallel polarized as they leave the optical interferometer 210 and enter the directional element 224. In this case the system operates exactly the same way as when the mirrors 218, 220 of the interferometer 210 are implemented as Faraday mirrors. In accordance with another aspect of the invention, the polarization controller is aligned such that the two portions of the optical radiation are polarized orthogonally as they leave the optical interferometer 210, so the system becomes a so-called "cross-polarization" OCR/OCT device. In the latter case, the frequency domain optoelectronic registering unit 248 registers a combination optical radiation responsive only to a portion of the reflected optical radiation that is depolarized by the sample 230. The non-depolarized portion of the optical radiation reflected from the sample 230 does not produce interference fringes and is not registered. Cross-polarization OCT is well known to create enhanced contrast in some biotissues.

A slow delay line, analogous to that used in the embodiment of FIG. 1 to control the axial position of the observation zone can be introduced in any of the arms of the optical unit 210 (not shown in the drawing).

In one preferred embodiment, analogous to that of FIG. 1, the source 202 of optical radiation is made narrowband and tunable, whereas the frequency domain optoelectronic registering unit 248 includes at least one photodetector connected with the data processing and displaying unit (not shown in FIG. 2). In another embodiment, the source 202 is broadband and implemented as a low-coherence source of optical radiation. In this embodiment, a spectrometer, instead of a single photodiode, is used in the frequency domain optoelectronic registering unit 248, therefore parallel registration is performed instead of sequential. A skilled artisan will recognize that no optical path difference scanning is necessary in these embodiments, and therefore, no optical path difference scanning is performed.

Figure 3:
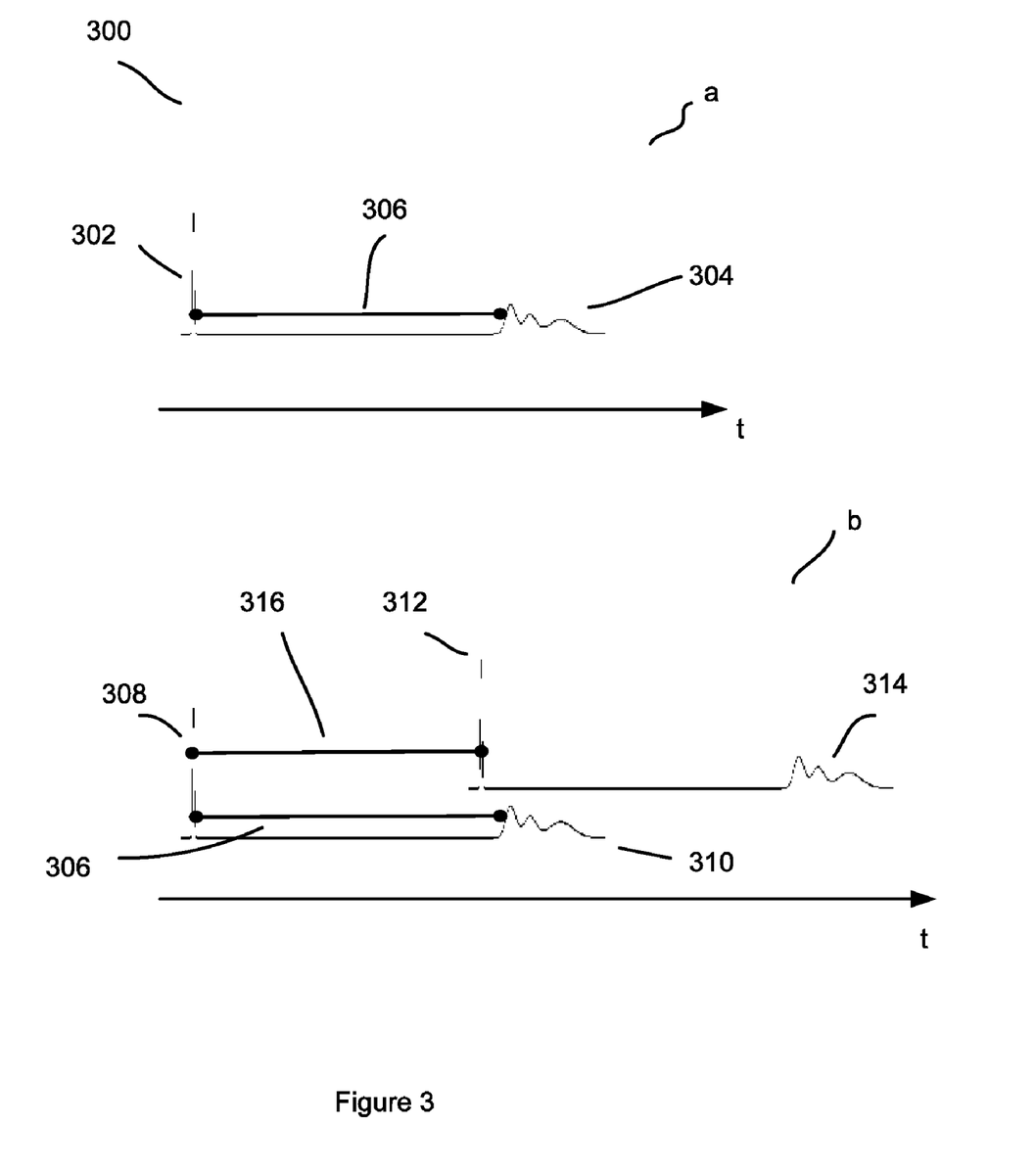
FIG. 3 is an illustration of producing a combination optical radiation in an embodiment of the invention shown in FIG. 1.

Turning now to FIG. 3, there is shown an illustration 300 of producing a combination optical radiation in an embodiment of the invention depicted in FIG. 1. For illustration purposes the optical radiation is represented by an imaginary short pulse propagating therethrough and placed along a time axis t in FIG. 3. Thus, FIG. 3a illustrates the optical radiation returning from the delivering device 110 (optical fiber probe 126) to enter the optical unit 132 (optical interferometer 138) through the directional element 106 (see FIG. 1). As depicted in FIG. 3, the reference portion 302 of the optical radiation has a time shift with respect to the sample portion 304, the time shift being defined by a reference offset 306. FIG. 3b illustrates two replicas of the optical radiation shown in FIG. 3a. The two replicas are depicted at the directional coupler 140 after they have propagated in the optical interferometer 138 in the forward and backward direction along respective optical paths. As seen in FIG. 3b, the reference portion 308 of one replica has a time shift with respect to the sample portion 310 of the same replica, the time shift being defined by the reference offset 306. The reference portion 312 of the other replica has a time shift with respect to the sample portion 314 of the same replica, the time shift being also defined by the reference offset 306. The two replicas are shifted with respect to each other, the shift being defined by the interferometer offset 316. As discussed in detail above, the value of the interferometer offset being in the vicinity of the value of the reference offset, the two portions interfere a very similar way to the traditional separate path optical coherence reflectometer. At the same time, no depth ambiguity problem arises since the optical path difference for the interfering reference and any part of sample portion belonging to the in depth range of interest of the two replicas of the optical radiation is not reduced to zero.

Figure 4:
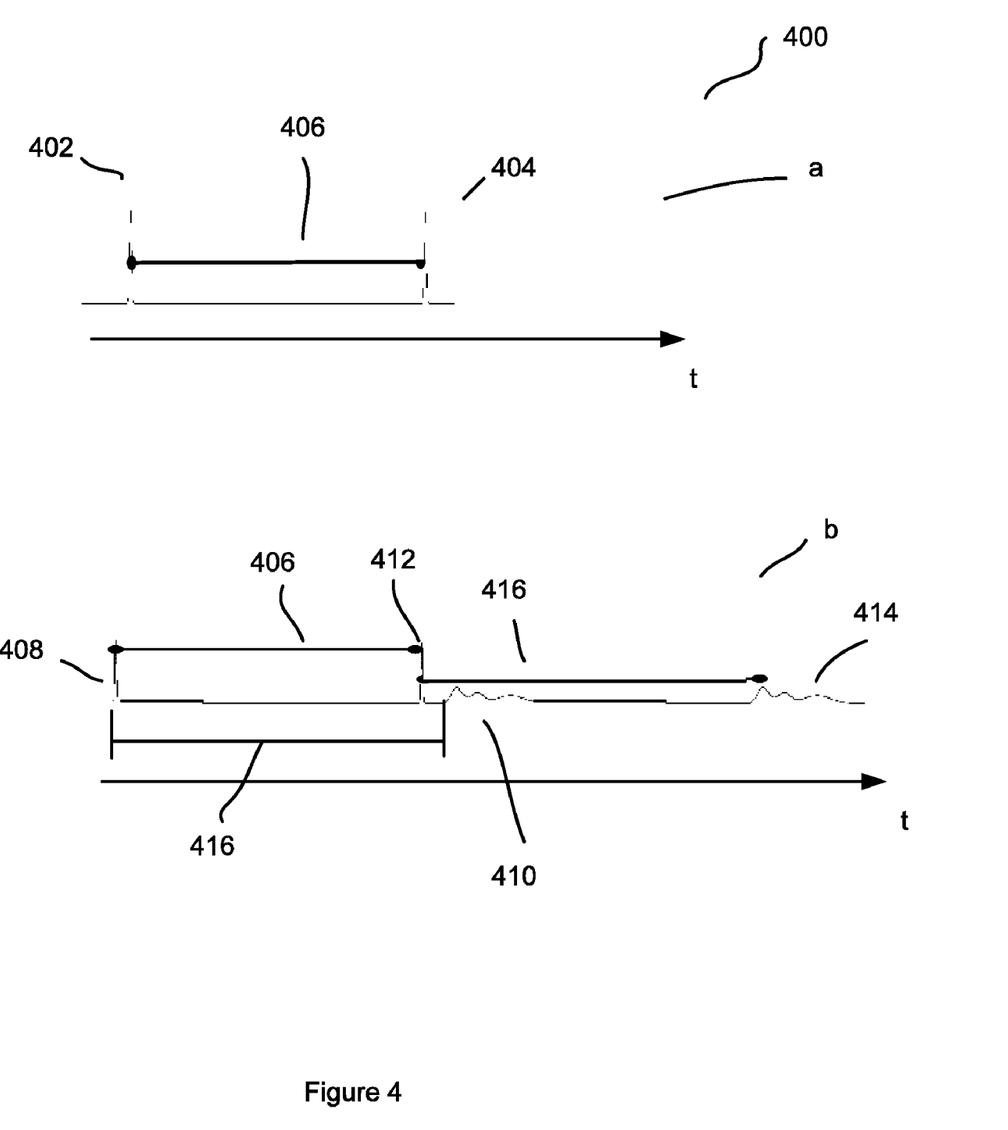
FIG. 4 is an illustration of producing a combination optical radiation in an embodiment of the invention shown in FIG. 2.

Turning now to FIG. 4, there is shown an illustration 400 of producing a combination optical radiation in an embodiment of the invention depicted in FIG. 2. For illustration purposes the optical radiation is represented by an imaginary short pulse propagating therethrough and placed along a time axis t in FIG. 4. Thus, FIG. 4a illustrates the optical radiation entering the delivering device 226 (optical fiber probe 242) through the directional element 224 of FIG. 2, after the optical radiation is divided into two portions (replicas) shifted along the time axis by the optical interferometer 210. The two replicas are illustrated in FIG. 4a as respective short pulses 402 and 404. As will be recognized by a skilled artisan, the time shift between the two replicas of the optical radiation is defined by the interferometer offset 406. FIG. 4b illustrates the two replicas after each of them was split into two portions (a reference portion and a sample portion) by the reference reflector 234 (the tip 244 of the optical fiber 246 of the optical fiber probe 242). As shown in FIG. 4b, the reference portion 408 of the first replica has a shift (reference offset 416) with respect to the sample portion 410 of the same replica. Also, the reference portion 412 of the first replica has a shift (reference offset 416) with respect to the sample portion 414 of the same replica. Those skilled in the art will appreciate that reference portion of one replica interferes with the sample portion of the other replica in the same manner as discussed with respect to FIG. 3.

The foregoing description of the preferred embodiments of the subject application has been presented for purposes of illustration and description. It is not intended to be exhaustive or to limit the subject application to the precise form disclosed. Obvious modifications or variations are possible in light of the above teachings. The embodiments were chosen and described to provide the best illustration of the principles of the subject application and its practical application to thereby enable one of ordinary skill in the art to use the subject application in various embodiments and with various modifications as are suited to the particular use contemplated. All such modifications and variations are within the scope of the subject application as determined by the appended claims when interpreted in accordance with the breadth to which they are fairly, legally and equitably entitled.

What is claimed is:

1. A common path frequency domain optical coherence reflectometer comprising:
    a source of an optical radiation;
    a directional element;
    a delivering device adapted to form and deliver an optical radiation beam to a sample, the delivering device having a proximal part and a distal part, the distal part of the delivering device including a reference reflector;
    an optical unit, optically coupled with the proximal part of the delivering device through the directional element;
    an optical element for producing a combination optical radiation by combining an optical radiation returning from the sample with a reference optical radiation reflected from the reference reflector; and
    a frequency domain optoelectronic registering unit adapted to register the combination optical radiation and including a data processing and displaying unit;
    wherein the optical unit includes an optical element for splitting an incoming optical radiation into two portions, and at least two optical paths adapted for the respective portions of the optical radiation to propagate therethrough; and
    wherein the at least two optical paths have an optical path length difference.

2. The common path frequency domain optical coherence reflectometer of claim 1 further specified by a longitudinal range of interest, the longitudinal range of interest including a proximal boundary and a distal boundary, and at least partially overlapping with the sample, and further having an optical path length difference of a first value for the optical radiation beam propagating to the reference reflector and to the proximal boundary of the longitudinal range of interest, and having an optical path length difference of a second value for the optical radiation beam propagating to the reference reflector and to the distal boundary of the longitudinal range of interest, wherein the value of the optical path length difference for the two portions of the optical radiation propagating in the optical unit is one of the following: less than the first value, and exceeds the second value.

3. The common path frequency domain optical coherence reflectometer of claim 1 further specified by a longitudinal range of interest, the longitudinal range of interest including a proximal boundary and a distal boundary, and at least partially overlapping with the sample, and further having an optical path length difference of a first value for the optical radiation beam propagating to the reference reflector and to the proximal boundary of the longitudinal range of interest, and having an optical path length difference of a second value for the optical radiation beam propagating to the reference reflector and to the distal boundary of the longitudinal range of interest, wherein the value of the optical path length difference for the two portions of the optical radiation propagating in the optical unit lies between the first and second values, and wherein at least one of the optical paths of the optical unit further includes a device adapted for substantially eliminating at least one of mirror ambiguity, DC artifacts, and auto-correlation artifacts.

4. The common path frequency domain optical coherence reflectometer of claim 1 wherein the optical unit is in optical communication with the source of optical radiation through the directional element, and wherein the reference reflector serves as the optical element for producing the combination optical radiation.

5. The common path frequency domain optical coherence reflectometer of claim 4 wherein the optical unit is an optical interferometer, and wherein the at least two optical paths of the optical unit are arms of the optical interferometer.

6. The common path frequency domain optical coherence reflectometer of claim 5 wherein each arm of the optical interferometer includes a Faraday mirror at its end.

7. The common path frequency domain optical coherence reflectometer of claim 5 wherein at least one of the arms of the optical interferometer includes a regular mirror at its end, and wherein at least one arms of the optical interferometer includes a polarization controller.

8. The common path frequency domain optical coherence reflectometer of claim 1 wherein the delivering device is in optical communication with the source of optical radiation through the directional element, and wherein the optical unit further includes the optical element for producing the combination optical radiation.

9. The common path frequency domain optical coherence reflectometer of claim 8 wherein the optical element of the optical unit for splitting an incoming optical radiation into two portions of the optical radiation further serves as the optical element for producing the combination optical radiation.

10. The common path frequency domain optical coherence reflectometer of claim 9 wherein the optical unit is an optical interferometer, wherein the at least two optical paths of the optical unit are arms of the optical interferometer, and wherein the arms of the optical interferometer each include a Faraday mirror at its end.

11. The common path frequency domain optical coherence reflectometer of claim 1 wherein at least one of the optical paths of the optical unit further includes a device adapted for substantially eliminating at least one of mirror ambiguity, DC artifacts, and autocorrelation artifacts.

12. The common path frequency domain optical coherence reflectometer of claim 11 wherein at least one of the optical paths of the optical unit further includes means adapted for improving a signal-to-noise ratio of the common path frequency domain optical coherence reflectometer.

13. The common path frequency domain optical coherence reflectometer of claim 12, wherein the means adapted for improving the signal-to-noise ratio includes one of a phase modulator, and a frequency modulator.

14. The common path frequency domain optical coherence reflectometer of claim 1 wherein at least one of the optical paths of the optical unit further includes means adapted for improving a signal-to-noise ratio of the common path frequency domain optical coherence reflectometer.

15. The common path frequency domain optical coherence reflectometer of claim 14 wherein the means adapted for improving the signal-to-noise ratio includes one of a phase modulator, and a frequency modulator.

16. The common path frequency domain optical coherence reflectometer of claim 11, wherein the optical device adapted for substantially eliminating at least one of mirror ambiguity, DC artifacts, autocorrelation artifacts, is further adapted for improving the signal-to-noise ratio.

17. The common path frequency domain optical coherence reflectometer of claim 16 wherein the means adapted for substantially eliminating at least one of mirror ambiguity, DC artifacts, autocorrelation artifacts, and improving the signal-to-noise ratio includes one of a phase modulator, and a frequency modulator.

18. The common path frequency domain optical coherence reflectometer of claim 1 wherein the source of optical radiation is made tunable, and wherein the frequency domain optoelectronic registering unit includes at least one photodetector connected with the data processing and displaying unit.

19. The common path frequency domain optical coherence reflectometer of claim 1 wherein the source of optical radiation is a low-coherence source of optical radiation, and wherein the frequency domain optoelectronic registering unit includes a spectrometer connected with the data processing and displaying unit.

20. The common path frequency domain optical coherence reflectometer of claim 1 wherein the delivering device is an optical fiber probe.

21. The common path frequency domain optical coherence reflectometer of claim 20 wherein the optical fiber probe comprises an optical fiber including a tip, and wherein the tip of the optical fiber serves as the reference reflector.

22. The common path frequency domain optical coherence reflectometer of claim 1 further including means for changing relative positions of the optical radiation beam being delivered to the sample, and the sample, wherein the common path frequency domain optical coherence reflectometer is part of a common path frequency domain device for optical coherence tomography.

23. The common path frequency domain optical coherence reflectometer of claim 22 wherein the source of optical radiation is made tunable, whereas the frequency domain optoelectronic registering unit includes at least one photodetector connected with the data processing and displaying unit.

24. The common path frequency domain optical coherence reflectometer of claim 22 wherein the source of optical radiation is a low-coherence source of optical radiation, and wherein the frequency domain optoelectronic registering unit includes a spectrometer connected with the data processing and displaying unit.

25. A common path frequency domain optical coherence tomography device comprising:
   a source of optical radiation;
   a directional element;
   an optical fiber probe adapted to form and deliver an optical radiation beam to a sample and comprising an optical fiber, the optical fiber including a tip that serves as a reference reflector;
   an optical interferometer being in optical communication with the optical fiber probe through the directional element;
   an optical element for producing a combination optical radiation by combining an optical radiation returning from the sample with a reference optical radiation reflected from the tip of the optical fiber of the optical fiber probe;
   means for changing relative positions of the optical radiation beam being delivered to the sample, and the sample; and
   a frequency domain optoelectronic registering unit adapted to register the combination optical radiation and including a data processing and displaying unit;
   wherein the optical interferometer includes an optical element for splitting an incoming optical radiation into two portions, and at least two arms adapted for the respective portions of the optical radiation to propagate therethrough; and
   wherein the at least two arms of the optical interferometer have an optical path length difference and each include a mirror at their end.

26. The common path frequency domain optical coherence tomography device of claim 25, wherein at least one arm of the optical interferometer includes an optical device adapted for substantially eliminating at least one of mirror ambiguity, DC artifacts, and autocorrelation artifacts, and adapted for improving a signal-to-noise ratio of the common path frequency domain optical coherence tomography device.

27. The common path frequency domain optical coherence tomography device of claim 26 wherein the optical device adapted for substantially eliminating at least one of mirror ambiguity, DC artifacts, autocorrelation artifacts, and adapted for improving the signal-to-noise ratio includes one of a phase modulator, and a frequency modulator.

28. The common path frequency domain optical coherence tomography device of claim 25 further specified by a longitudinal range of interest including a proximal boundary and a distal boundary, and at least partially overlapping with the sample, and further having an optical path length difference of a first value for the optical radiation beam propagating to the tip of the optical fiber of the optical fiber probe and to the proximal boundary of the longitudinal range of interest, and having an optical path length difference of a second value for the optical radiation beam propagating to the tip of the optical fiber of the optical fiber probe and to the distal boundary of the longitudinal range of interest, wherein the value of the optical path length difference of the at least two arms of the optical interferometer is one of the following: less than the first value, and exceeds the second value.

29. The common path frequency domain optical coherence reflectometer of claim 25 wherein the optical interferometer is in optical communication with the source of optical radiation through the directional element, and wherein the tip of the optical fiber probe serves as the optical element for producing the combination optical radiation.

30. The common path frequency domain optical coherence reflectometer of claim 29 wherein each arm of the optical interferometer includes a Faraday mirror.

31. The common path frequency domain optical coherence reflectometer of claim 29 wherein at least one arm of the optical interferometer includes a regular mirror, and wherein at least one arm of the optical interferometer includes a polarization controller.

32. The common path frequency domain optical coherence reflectometer of claim 25 wherein the optical fiber probe is in optical communication with the source of optical radiation through the directional element, wherein the optical interferometer further includes the optical element for producing the combination optical radiation, and wherein each arm of the optical interferometer includes a Faraday mirror.

33. The common path frequency domain optical coherence reflectometer of claim 32 wherein the optical element of the optical interferometer for splitting an incoming optical radiation into two portions of the optical radiation further serves as the optical element for producing the combination optical radiation.

34. The common path frequency domain optical coherence tomography device of claim 25 wherein the source of optical radiation is made tunable, and wherein the frequency domain optoelectronic registering unit includes at least one photodetector connected with the data processing and displaying unit.

35. The common path frequency domain optical coherence tomography device of claim 25 wherein the source of optical radiation is a low-coherence source of optical radiation, and wherein the frequency domain optoelectronic registering unit includes a spectrometer connected with the data processing and displaying unit.

* * * * *